United States Patent [19]

Gosselin

[11] Patent Number: 5,304,191

[45] Date of Patent: Apr. 19, 1994

[54] SURGICAL INSTRUMENT WITH ROTATABLE INDEXING FOOTED ATTACHMENT

[75] Inventor: Norman J. Gosselin, Eagle Mtn. Lake, Tex.

[73] Assignee: Midas Rex Pneumatic Tools, Inc., Fort Worth, Tex.

[21] Appl. No.: 17,021

[22] Filed: Feb. 12, 1993

[51] Int. Cl.⁵ .............................................. A61B 17/16
[52] U.S. Cl. ...................................... 606/172; 30/276
[58] Field of Search ...................... 606/172, 176-179; 30/276, 286, 370

[56] References Cited

U.S. PATENT DOCUMENTS

| | | |
|---|---|---|
| 2,429,356 | 10/1947 | Hicks . |
| 3,223,088 | 12/1965 | Barber et al. . |
| 3,308,828 | 3/1967 | Pippin . |
| 3,750,671 | 8/1973 | Hedrick . |
| 4,071,030 | 1/1978 | Hedrick . |
| 4,340,060 | 7/1982 | Berke et al. . |

Primary Examiner—Stephen C. Pellegrino
Assistant Examiner—William W. Lewis
Attorney, Agent, or Firm—James E. Bradley; Mark D. Perdue

[57] ABSTRACT

A surgical instrument includes a motor, a dissecting tool coupled to the motor for rotation about an axis of the motor, the motor further including a base at one end thereof. The motor is further provided with an elongate member extending from the base and parallel to the motor axis. A foot member extends laterally from a terminal end of the elongate member for protecting selected portions of tissue from exposure to the cutting action of the dissecting tool. The surgical instrument is further provided with indexing means to permit selective rotation of the elongate member relative to base from one of a plurality of angular positions to another of the plurality of angular positions, and to secure the elongate member in a selected angular position.

13 Claims, 2 Drawing Sheets

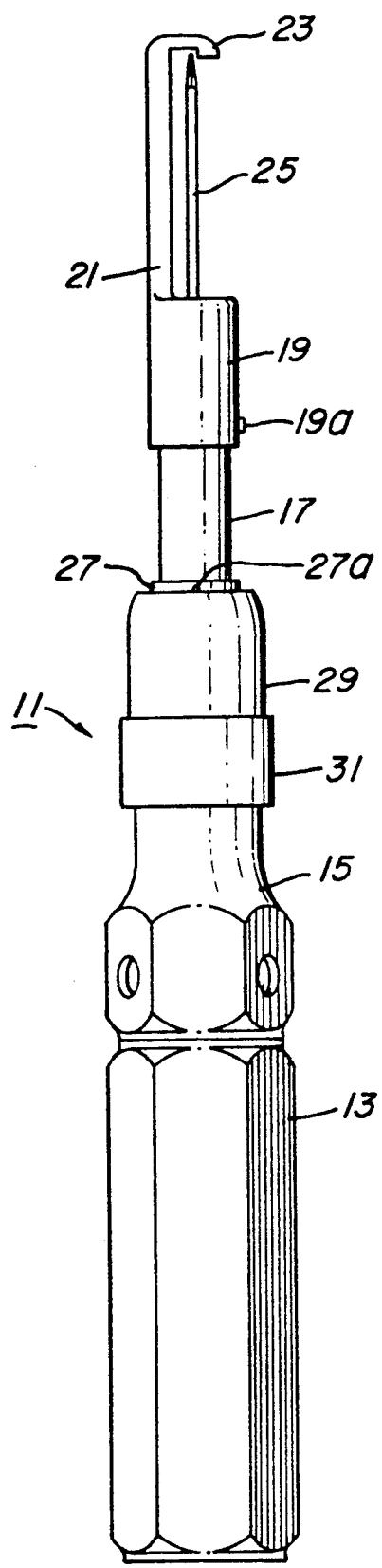
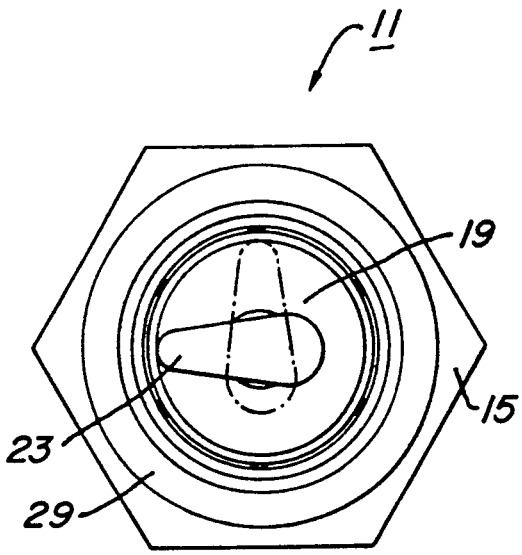
Fig. 2
Fig. 1

SURGICAL INSTRUMENT WITH ROTATABLE INDEXING FOOTED ATTACHMENT

BACKGROUND OF THE INVENTION

1. Field of the Invention

The present invention relates broadly to surgical instruments for use in the dissection of tissue. More specifically, the present invention relates to surgical instruments for rotating dissecting tools and footed attachments therefor for the purpose of protecting sensitive tissue from exposure to the cutting action of the dissecting tool while cutting bone.

2. Summary of the Prior Art

Surgical instruments for rotating dissection tools to dissect bone long have been employed in the medical arts. Such surgical instruments have particularly utility when used as craniotomes. Craniotomes are surgical instruments employed in the surgical procedure known as craniotomy. Craniotomy involves opening the skull so that access thereto may be had to perform neurosurgery or the like. Typically, craniotomy is performed to remove a section of skull by drilling a series of holes through the cranial bones at points defining the perimeter of the cranial section to be removed. Next, the series of holes are connected by a craniotome in a procedure not unlike the use of a conventional jigsaw.

A danger present in such craniotomies is the risk of penetrating too far into the skull, piercing the dura (the membrane protecting the brain) and into the brain itself. Obviously, if the dura, and the brain underlying it, are penetrated, very serious damage can occur. Consequently, surgical instruments for use in craniotomies are provided with footed attachments or duraguards for protecting the dura and underlying brain from the cutting action of the dissecting tool. Duraguards and similar attachments are shown in U.S. Pat. No. 2,429,356, Oct. 21, 1947, to Hicks; U.S. Pat. No. 3,223,088, Dec. 14, 1965, to Barber et al.; U.S. Pat. No. 3,308,828, Mar. 14, 1967, to Pippin; and U.S. Pat. No. 3,340,060, Jul. 20, 1982 to Berke et al.

One drawback to most prior-art duraguards or footed attachments is that they are fixed relative to the surgical instrument itself. Typically, it is necessary to turn the direction of cutting of the surgical instrument to complete the dissection of a segment of the cranium. This turning necessitates rotation of the entire surgical instrument, which cannot be accomplished easily in the relatively narrow kerf formed by the dissecting tool. Thus, a plurality of pilot holes initially must be bored in the skull to accommodate the turning of the surgical instrument. Prior-art U.S. Pat. No. 4,071,030, Jan. 31, 1978, to Hedrick, discloses a duraguard that is freely rotatable, on ball bearings, relative to the remainder of the surgical instrument. However, because the duraguard is freely rotatable, such a prior-art duraguard is susceptible to undesirable rotation and migration from behind the dissecting tool. If such undesirable rotation or migration occurs, the ability of the user to guide the surgical instrument may be impaired, and the possibility of mistakes increased.

A need exists for a footed attachment or duraguard for use with a surgical instrument for rotating a dissecting tool, wherein the footed attachment is provided with indexing means to permit selective rotation of the footed member or duraguard from one angular position to another, and wherein the indexing means is further provided with a means to secure the footed member or duraguard in any number of selected angular positions relative to the surgical instrument.

SUMMARY OF THE INVENTION

It is a general object of the present invention to provide a surgical instrument having a footed attachment or duraguard that is capable of being rotated into a plurality of angular positions and secured against rotation therein, wherein the dissection of bone with such an instrument is facilitated.

This and other objects of the present invention are accomplished by providing a surgical instrument including a motor, a dissecting tool coupled to the motor for rotation about an axis of the motor, the motor further including a base at one end thereof. The motor is further provided with an elongate member extending from the base and parallel to the motor axis. A foot member extends laterally from a terminal end of the elongate member for protecting selected portions of tissue from exposure to the cutting action of the dissecting tool. The surgical instrument is further provided with indexing means to permit selective rotation of the elongate member relative to base from one of a plurality of angular positions to another of the plurality of angular positions, and to secure the elongate member in a selected angular position.

According to a preferred embodiment of the present invention, the indexing means comprises a ball retainer member disposed about the elongate member and within the base, and at least one ball member carried by the ball retainer member. The elongate member is further provided with at least one ball receptacle to at least partially receive the at least one ball member. A cam member is coupled to the base for axial movement relative to the ball retainer member to selectively engage and urge the ball member into locking engagement with the ball receptacle, wherein the elongate member is secured against rotation relative to the base. The cam member is further provided with a biasing member to urge the cam member normally into engagement with the ball member, wherein the elongate member normally is secured against rotation relative to the base.

Other objects, features and advantages of the present invention will become apparent to those skilled in the art with reference to the drawings and detailed description, which follow.

BRIEF DESCRIPTION OF THE DRAWINGS

FIG. 1 is an elevation view of a surgical instrument including a rotatable footed member according to the present invention.

FIG. 2 is a plan view of the surgical instrument of FIG. 1, illustrating, in solid and phantom lines, two of the plurality of angular positions of the elongate member and foot member relative to the surgical instrument.

DETAILED DESCRIPTION OF PREFERRED EMBODIMENT

Figure 3:
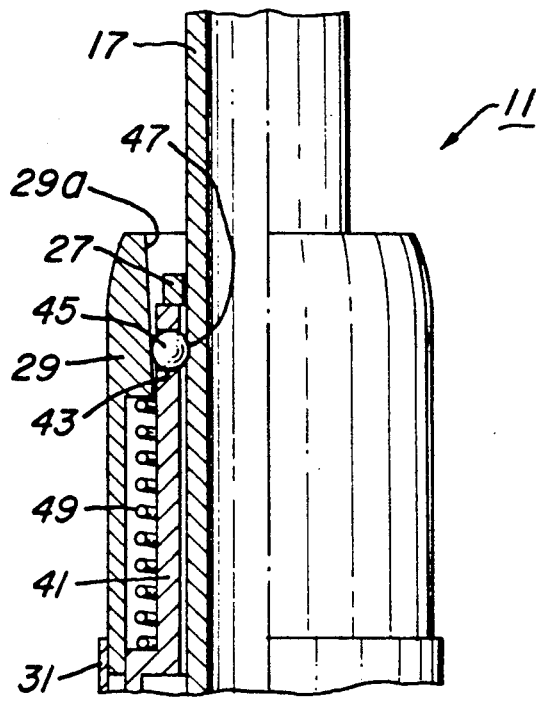
FIG. 3 is a partial, one-quarter, longitudinal section view of the surgical instrument of FIG. 1 illustrating the indexing means in a secured position.

Referring now to the Figures and particularly to FIG. 1, the reference numeral 11 generally designates a surgical tool according to the present invention. Surgical tool 11 comprises a motor 13, in this case a fluid-powered motor adapted for connection to a fluid pressure source (not shown). Motor 13 has an axis of rotation 13a. A base 15 is coupled by threads to motor 13. Base 15 provides a shroud or covering for the dissecting tool-receiving chuck (not shown) of motor 13.

A tubular portion 17 of an elongate member assembly extends from base 15 substantially coaxially with axis of rotation 13a. A footed attachment or duraguard 19 is secured to tubular portion 17 of the elongate member by means of a set screw 19a. Duraguard 19 is further provided with a leg member 21, which extends from duraguard 19 substantially parallel to and spaced apart from axis of rotation 13a. A foot member 23 extends laterally from a terminal end of leg member 21.

Surgical tool is further provided with a dissecting tool 25. Dissecting tool 25 is rotated about axis of rotation 13a by motor 13, in this case responsive to fluid pressure from a fluid pressure source (not shown).

A retainer ring 27 is secured to tubular portion 17 of the elongate member by set screw 27a. Retainer ring 27 serves to prevent elongate member from telescoping or retracting within base 15.

Surgical instrument 11 is further provided with an indexing means including cam member 29 and shroud 31. The detailed structure and operation of the indexing means will be described hereinafter.

FIG. 2 depicts, in plan view, surgical instrument il of FIG. 1, viewed from above. Illustrated are base 15, footed attachment or duraguard 19, foot member 23, and cam member 29. FIG. 2 illustrates the rotation of footed member 23, along with leg member 21 (shown in FIG. 1), relative to base 15. As is illustrated, the indexing means provides the ability to rotate foot member 23 from a first angular position (shown in object line) to a second selected angular position (shown in phantom line).

Figure 4:
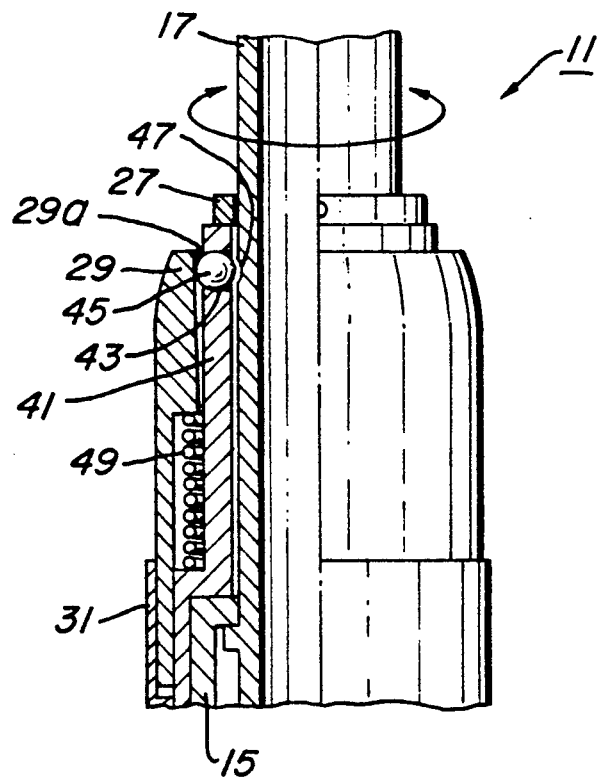
FIG. 4 is a partial, one-quarter, longitudinal section view of the surgical instrument of FIG. 1 depicting the indexing means in a rotatable position.

Referring now to FIGS. 3 and 4, the indexing means of surgical instrument 11 according to the present invention is illustrated in partial, one-quarter, longitudinal section. A ball keeper or ball retainer sleeve member 41 is disposed between base 15 and tubular portion 17 of the elongate member. Ball keeper or retainer sleeve member 41 is secured to base 15 by conventional means, and tubular portion 17 of elongate member is rotatably disposed within ball keeper 41. Ball keeper 41 is provided with at least one ball retainer aperture 43, which releasably receives at least one ball member 45. Ball retainer aperture 43 is provided with semi-spherical walls to receive ball member 45, yet prevent ball member 45 from passing entirely through ball retainer aperture 43.

At least one ball recess or receptacle cavity 47 is provided in tubular portion 17 of the elongate member. Ball receptacle cavity 47 is a semi-spherical cavity adapted to receive at least a portion of the outer surface of ball member 45.

A biasing means, preferably a coil spring, 49 is provided between base 15 and cam member 29 to urge cam member 29 normally axially upward into engagement with ball member 45, which in turn is maintained in engagement with ball receptacle cavity 47. Cam member 29 is provided with an inclined inner surface 29a to facilitate engagement between cam member 29 and ball member 45. Engagement between inclined surface 29a and ball member 45 retains cam member 29 in sliding engagement over base 15 and base-protecting shroud 31.

Ball keeper or retainer sleeve member 41, ball retainer apertures 43, ball members 45, and ball receptacle cavities 47 cooperate to form a locking means to secure tubular portion 17 of the elongate member against rotation relative to base 15

FIG. 4 illustrates the indexing means of FIG. 3 in an unlocked position, wherein tubular portion 17 of the elongate member, as well as footed attachment or duraguard 19, leg member 21, and foot member 23 are permitted to rotate relative to base 15. In the unlocked position, cam member 29 is moved axially downwardly and away from ball members 45. The circumferentially spaced-apart relationship of ball member 45 according to a preferred embodiment of the present invention is apparent with cam member 29 axially displaced relative to ball members 45. Each ball member 45 has a corresponding ball receptacle cavity 47, circumferentially spaced about tubular portion 17 of the elongate member. The number of ball receptacle cavities 47 may be selected to determine the number of angular positions in which tubular portion 17 can be constrained against rotation relative to base 15. If more ball receptacles cavities 47 are provided, more angular positions are available in which to lock tubular portion 17 against rotation relative to base 15. Of course, the maximum number of ball receptacles cavities 47 that may be provided is limited by the dimensions of ball receptacles cavities 47, and the circumference of tubular portion 17.

In the unlocked position shown, cam member 29 is displaced axially away from ball members 45 and biasing member 49 is compressed. With cam member 29 disengaged from ball members 45, locking engagement between ball members 45 and ball receptacles 47 is lost, and tubular portion 17 is free to rotate relative to base 15. Balls 45 are free to move radially outward from engagement with recesses 47 a short distance Cam member 29 may be released, wherein biasing member 49 urges inclined surface 29a of cam member 29 into engagement with ball members 45, which in turn engage ball retainer cavities 47 to lock tubular portion 17 against rotation relative to base 15 (as shown in FIG. 4).

With reference now to FIGS. 1 through 4, the operation of surgical instrument 11 will be described. The operation described is a craniotomy, however, surgical instrument 11 according to the present invention is useful in any number of surgical or dissection procedures in which it is advantageous to protect selected tissues from the cutting action of dissecting tool 25. For purposes of this description, it is assumed that any necessary pilot holes are already drilled in the cranium using a separate surgical instrument (not shown).

Surgical instrument 11 including footed attachment or duraguard 19 is provided. Foot member 23, leg member 21, and dissecting tool 25 are inserted into the cranium (not shown) through the pilot hole (not shown). Foot member 23 protects the dura and underlying brain (not shown) from the cutting action of dissecting tool 25.

Motor 13 then is energized, preferably by fluid pressure, and dissecting tool 25 is rotated about motor axis of rotation 13a. Dissection or cutting of cranial bones (not shown) then is commenced. At some point in the dissection, it becomes necessary for the user or surgeon to change the direction in which dissection or cutting of cranial bones is performed. At this point, cam member is retracted from engagement with ball members 45 by exertion of manual pressure on cam member 29 sufficient to overcome the biasing force supplied by biasing member 49. Tubular portion 17 of elongate member, as well as footed attachment or duraguard 19, including leg member 21 and foot member 23, then is free to rotate relative to base 15 from the original angular position (shown in solid line in FIG. 2) to another angular position (whose in phantom line in FIG. 2). Depending on the number of ball receptable cavities 47 provided on tubular portion 17 of the elongate member, foot member 23 may be rotated to any number of angular positions relative to base 15. Upon indexing and rotation of foot member 23 to the desired angular position, dissection or cutting of cranial bone (not shown) may be continued in a different and selected direction.

Thus, surgical instrument 11 is operable in a plurality of modes of operation, including a locked position or mode of operation in which footed attachment or duraguard 19 is secured against rotation relative to base 15. Another mode of operation is the unlocked position or mode of operation in which cam member 29 is axially displaced from engagement with ball members 45, which permits free rotation of tubular portion 17 and footed attachment or duraguard 19 relative to base 15. Footed attachment or duraguard 19 may be returned to the locked position or mode of operation after an advantageous orientation of foot member 23 and leg member 21 relative to base 15 is obtained.

The surgical instrument including a footed attachment or duraguard according to the present invention possesses a number of advantages over prior-art surgical instruments. One advantage of the surgical instrument according to the present invention is that an excessive number of pilot holes need not be formed in the cranium or other tissue to be dissected. Elimination of the necessity for a plurality of pilot holes reduces the probability of undesirable penetration of the dura and underlying brain during formation of the pilot holes. Another advantage of the present invention is that an indexed, rotatable, footed attachment or duraguard is provided, which permits the user to select from a plurality of angular positions of the footed attachment of duraguard relative to the base and motor of the surgical instrument. This advantage results in an easily manipulated surgical instrument, which minimizes user fatigue during critical and minute surgical operations. The ability to manipulate the duraguard or footed attachment relative to the base and motor also speeds dissection procedures, an important advantage because time often is of the essence during surgical procedures.

The invention has been described with reference to a preferred embodiment thereof. Those skilled in the art will appreciate that the invention is subject to variation and modification without departing from the scope thereof.

I claim:

1. In a surgical instrument including a motor, a dissecting tool coupled to the motor for rotation about an axis of the motor, the motor further including a base at an end thereof, the improvement comprising:

an elongate member extending from the base and parallel to the axis, the elongate member having a terminal end;

a foot member extending laterally from the terminal end of the elongate member for protecting selected portions of tissue form exposure to the dissecting tool;

indexing means to permit selective rotation of the elongate member relative to the base from one of a plurality of angular positions to another of the plurality of angular positions, and to secure the elongate member in a selected angular position; and a cam means for selectively actuating the indexing means from a locked position to an unlocked position in response to movement of the ca means relative to the elongate member.

2. In a surgical instrument including a motor, a dissecting tool coupled to the motor for rotation about an axis of the motor, the motor further including a base at an end thereof, the improvement comprising:

an elongate member extending from the base and parallel to the axis, the elongate member having a terminal end;

a foot member extending laterally from the terminal end of the elongate member for protecting selected portions of tissue from exposure to the dissecting tool;

indexing means to permit selective rotation of the elongate member relative to the base form one of a plurality of angular positions to another of the plurality of angular positions, and to secure the elongate member in a selected angular position; and a locking means disposed between the base and the elongate member for locking the elongate member rigidly to the base in a locked position and for releasing the elongate member for rotation relative to the base in an unlocked position.

3. In a surgical instrument including a motor, a dissecting tool coupled to the motor for rotation about an axis of the motor, the motor further including a base at an end thereof, the improvement comprising:

an elongate member extending from the base and parallel to the axis, the elongate member having a terminal end;

a foot member extending laterally from the terminal end of the elongate member for protecting selected portions of tissue from exposure to the dissecting tool;

indexing means to permit selective rotation of the elongate member relative to the base form one of a plurality of angular positions to another of the plurality of angular positions, and to secure the elongate member in a selected angular position; and a locking means disposed between the base and the elongate member for locking the elongate member rigidly to the base in the locking position and for releasing the elongate member for rotation relative to the base int he unlocked position and a biasing means for urging the locking means normally into the locked position.

4. In a surgical instrument including a motor, a dissecting tool coupled to the motor for rotation about an axis of the motor, the motor further including a base at an end thereof, the improvement comprising:

an elongate member extending from the base and parallel to the axis, the elongate member having a terminal end;

a foot member extending laterally from the terminal end of the elongate member for protecting selected portions of tissue from exposure to the dissecting tool;

indexing means to permit selective rotation of the elongate member relative to the base form one of a plurality of angular positions to another of the plurality of angular positions, and to secure the elongate member in a selected angular position;

a locking member disposed between the base and the elongate member for locking the elongate member rigidly to the base in the locked position and for releasing the elongate member for rotation relative to the base int eh unlocked position; and a plurality of locking member recesses formed in the elongate member for engagement with the locking member in the locked position.

5. In a surgical instrument including a motor, a dissecting tool coupled to the motor for rotation about an axis of the motor, the motor further including a base at an end thereof, the improvement comprising:

an elongate member extending from and parallel to the base, the elongate member having a tubular portion disposed within the base, the elongate member further including a leg portion extending adjacent and parallel to the dissecting tool, the leg portion having a terminal end;

a foot member extending laterally from the terminal end of the leg portion for protecting selected portions of tissue from exposure to the dissecting tool;

locking means carried by the base and engageable with the tubular portion of the elongate member to selectively permit rotation of the elongate member relative to the base;

a cam member coupled to the locking means for axial movement to selectively engage the locking means; and a biasing means urging the cam member normally into engagement with the locking means.

6. The surgical instrument according to claim 5 wherein the tubular portion of the elongate member is provided with at least one lock recess for engagement with the locking means.

7. The surgical instrument according to claim 5 wherein the locking means comprises at least one ball member and a ball retainer sleeve having at least one ball keeper recess to at least partially receive the ball member.

8. The surgical instrument according to claim 5 wherein: the locking means includes:

a ball retainer sleeve having a plurality of circumferentially spaced ball keeper recesses formed therein; and a plurality of ball members for selective engagement with the tubular portion of the elongate member, wherein each of the ball members is carried by the ball keeper recesses; and a plurality of ball recesses formed in the tubular portion to receive and engage the plurality of ball members of the locking member.

9. In a surgical instrument including a motor, a dissecting tool coupled to the motor for rotation about an axis of the motor, the motor further including a base at an end thereof, the improvement comprising:

an elongate member mounted for rotation in and extending from and parallel to the base, the elongate member having a tubular portion disposed within the base, the elongate member further including a leg portion extending spaced apart from and parallel to the dissecting tool, the lege portion having a terminal end;

a foot member extending laterally from the terminal end of the leg portion for protecting selected portions of tissue from exposure to the dissecting tool;

a ball retainer sleeve disposed about the tubular portion of the elongate member and within the base;

at least one ball member carried by the ball retainer sleeve;

at least one ball receptacle cavity formed in the tubular portion of the elongate member for selective engagement with the at least one ball member;

a cam member coupled to the base for axial movement to selectively engage and urge the ball member into locking engagement with the ball receptacle cavity; and a biasing means to urge the cam member normally into engagement with the ball member.

10. The surgical instrument according to claim 5 wherein there are a plurality of ball receptacle cavities circumferentially spaced about the tubular portion of the elongate member, and the ball receptacle cavities are semi-spherical.

11. The surgical instrument according to claim 5 wherein the ball retainer sleeve is provided with a plurality of circumferentially spaced, generally circular ball retainer apertures, the ball retainer apertures having a semi-spherical interior surface to at least partially receive each ball member.

12. The surgical instrument according to claim 9 wherein the cam member comprises a cam sleeve disposed about the ball retainer member and the tubular portion of the elongate member and axially movable relative thereto, the sleeve having an inclined inner cam surface.

13. The surgical instrument according to claim 9 wherein the biasing means is a coil spring secured between the base and the cam member.

* * * * *